United States Patent [19]
Ward

[11] Patent Number: 4,953,567
[45] Date of Patent: Sep. 4, 1990

[54] PROPHYLACTIC DEVICE FOR USE WITH A TELEPHONE

[76] Inventor: Dale Ward, 3848 Charlotte Rd., Rex, Ga. 30273

[21] Appl. No.: 279,944

[22] Filed: Dec. 5, 1988

[51] Int. Cl.⁵ ............................................. A61F 13/00
[52] U.S. Cl. ................................... 128/851; 428/34.1; 150/165; 379/452; 383/907
[58] Field of Search .................... 128/851; 604/349; 150/154, 165; 379/451, 452; 383/907

[56] References Cited

U.S. PATENT DOCUMENTS

| | | | |
|---|---|---|---|
| D. 214,322 | 6/1969 | Velasquez | 379/451 X |
| 1,473,180 | 11/1923 | Foster | 150/165 X |
| 3,941,245 | 3/1976 | Oliverius | 206/438 |
| 4,438,300 | 3/1984 | Morse | 379/451 X |
| 4,515,841 | 5/1985 | Dyke | 428/35 |
| 4,781,709 | 11/1988 | Grubman | 604/349 |
| 4,794,920 | 1/1989 | Robichaud | 128/844 |

FOREIGN PATENT DOCUMENTS 2572607  5/1986  France ............................. 379/452

Primary Examiner—Richard J. Johnson
Assistant Examiner—Lynda M. Cofsky
Attorney, Agent, or Firm—Hurt, Richardson, Garner, Todd & Cadenhead

[57] ABSTRACT

A prophylactic device used in connection with a telephone which provides a telephone user with protection from indirect contact with previous users including a sleeve for covering the telephone receiver while in use and a detachable hand covering portion for avoiding direct hand contact with a telephone.

8 Claims, 3 Drawing Sheets

FIG 2
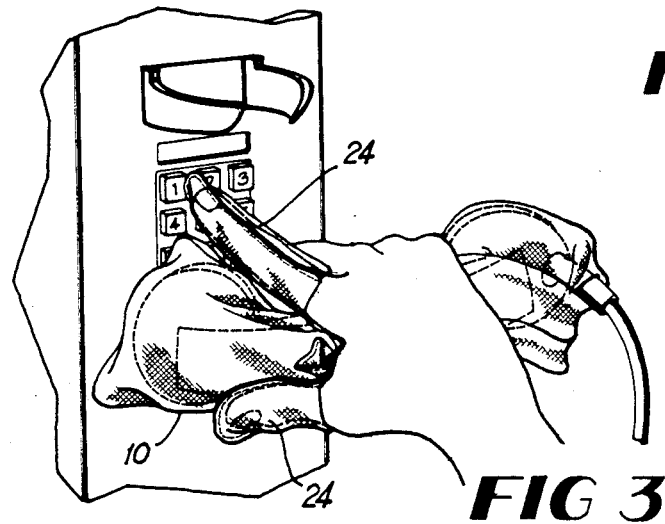
FIG 3
FIG 4

PROPHYLACTIC DEVICE FOR USE WITH A TELEPHONE

BACKGROUND OF THE INVENTION

1. Field of the Invention

The invention relates to a prophylactic device to be used in conjunction with a telephone such that a person using a telephone may protect themselves and others from germs which are collected on the receiver and dial of a telephone.

2. Description of the Prior Art

In the wake of the epidemic spread of contagious and potentially fatal diseases such as AIDS, there has been a surge in the popularity of prophylactic devices. For protection from casual contact with those who either carry or are afflicted with a variety of diseases of a contagious nature, people are resorting to protective devices of every sort. These devices include everything from condoms and toilet seat covers to surgical masks, rubber gloves and protective clothing.

One potential source of casual or indirect contact with carriers and manifestors of contagious and fatal diseases is through the use of the telephone, particularly those in public places. Most telephones are designed such that casual contact with the previous user is inevitable. The receiver is held pressed against the ear of the user, while the mouth piece is held within very close proximity to the user's mouth, collecting infectious saliva and germs from the breath as it is sprayed over the receiver. Persons with contagious skin diseases may have also last dialed the telephone or cradled the receiver between their shoulder and neck, leaving behind a skin residue to which the next user will inevitably be exposed.

For these reasons it is desirable to have a prophylactic device which can be used in conjunction with a telephone. Such a device is practical in protecting the telephone user from exposure to germs collected on the receiver and dial. People with particularly low resistance to disease may find such a device helpful in maintaining their health by avoiding direct contact with the telephone, while people with known infections may prevent the spread of their affliction within the general population by utilizing the present invention.

While it is known that prevention of the spread of disease is accomplished by reducing hand and mouth contact with others either directly or indirectly, most devices which are used to accomplish this are impractical in modern society. For instance, while rubber gloves and surgical masks may accomplish similar objectives in protecting telephone users from germs collecting on the receiver and dial pad, such devices are both socially unacceptable and burdensome to put on and take off. The use of a simple handkerchief is also known to cover a telephone, but does not fully protect the user from contact.

No known prior art contains all of the features and meets all of the objectives of the present invention, that is, to provide a simply designed prophylactic device to be used in conjunction with a telephone. The device should be portable, easy to use and reuse and socially acceptable to the general public. The prophylactic device can be either washable and reusable or disposable and can contain the further protection of an antiseptic placed within the device to further insure the user from exposure to germs.

SUMMARY OF THE INVENTION

It is therefore an object of the present invention to provide a prophylactic device to be used in conjunction with a telephone, which protects the user of the telephone from exposure to germs and infectious materials collected on the dial and receiver of the telephone.

It is a further object of the invention to provide a prophylactic device which can be manufactured at a low cost for mass production and mass distribution.

It is yet another object of the invention to provide a prophylactic device for use in connection with a telephone which is either washable and reusable and/or disposable.

The preferred embodiment of the prophylactic device for use with a telephone as described herein is characterized by a reinforced sleeve which is closed at the bottom end and open at the top end and is large enough to envelope a telephone receiver. Extending from the top portion of the sleeve, partially but not wholly surrounding the open end, is a manipulator comprised of a protective cover for the palm of the hand and a glove structure with a capacity for at least two fingers. The prophylactic device is made of a flexible thin material such as cloth, pliable plastic or tissue paper and can be internally coated with an antiseptic for further protection of the user.

Other advantages of the prophylactic device for use with a telephone will become apparent from the detailed description of the invention provided below.

BRIEF DESCRIPTION OF THE DRAWINGS

FIG. 2 is a perspective view showing a user depositing the receiver of a telephone into the present invention.

FIG. 3 illustrates the use of the present invention in dialing the telephone while avoiding contact with the dial pad.

FIG. 4 illustrates the user talking on a telephone with the receiver enveloped within the present invention.

DETAILED DESCRIPTION OF THE PREFERRED EMBODIMENT

A preferred exemplary embodiment of the invention is illustrated in FIGS. 1–6, wherein like numerals represent like parts. In this form of the invention, the prophylactic device for use with a telephone has a protective sleeve for enveloping the telephone receiver. A manipulator for the hand extends from the top of the sleeve for protecting the hand of the user while grasping the telephone receiver.

Figure 1:
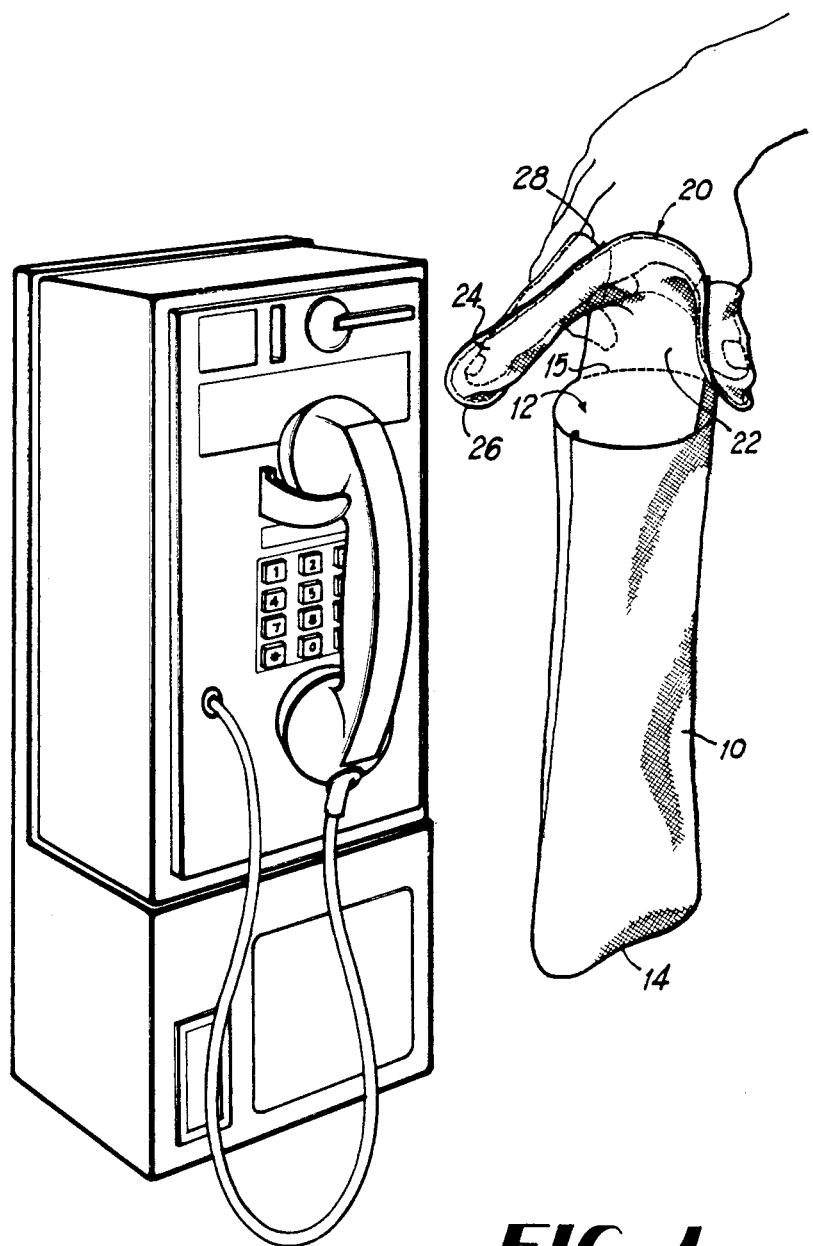
FIG. 1 is a perspective view of the prophylactic device shown with a user preparing to utilize the device in conjunction with a telephone.

FIG. 1 shows the prophylactic device for use with a telephone in accordance with the present invention. The prophylactic device has as the main portion, a sleeve 10 which has a open end 12 and a closed end 14. The sleeve 10 is of a dimension long enough and wide enough so that a conventionally sized telephone receiver can be slipped in through the open end 12 such that the ear piece of the receiver is deposited toward the closed end 14 of the sleeve 10, and the mouth piece of the telephone extends toward the open end 12. This allows the telephone cord to hang loosely from the opened end 12 of the sleeve as the user is talking into the receiver.

A manipulator 20 is connected to and extends from the open end 12 of the sleeve 10. The manipulator 20 extends around a portion of the open end 12 of the sleeve 10, equivalent to about half of the total circumference of the sleeve 10. The manipulator 20 has a palm protecting portion 22 and a plurality of finger extensions 24 attached to the top of palm protecting portion 22. The finger extensions are tubular extensions closed at their tips 26 and have insert slots 28 at the joinder of the finger extension 24 to the palm protection portion 22 of the manipulator 20. The insert slots 28 are located on the finger extensions on the opposite side of the manipulator 20 from where the manipulator 20 faces the sleeve 12. Stress points, particularly where the manipulator adjoins the sleeve opening 12, are reinforced to prevent tearing of the device during use.

As demonstrated in FIGS. 1-4, the prophylactic device is utilized by placing at least two diametrically opposed fingers inside the finger extensions 24 preferably either the thumb and index finger or the thumb and middle finger, such that the palm protecting portion 22 of the manipulator 20 covers the palm of the hand. The user then lifts the receiver from the telephone by placing the manipulator 20 around the neck of the receiver and depositing it inside the adjacent sleeve opening such that the ear piece falls to the bottom 14 of the sleeve 10. Depositing the receiver within the sleeve is demonstrated in FIG. 2.

Dialing can be achieved with the user's finger still covered by the finger extension 24 while holding the receiver when the dial pad is located on the main body of the telephone as demonstrated in FIG. 3. The manipulator 20 can also be releasably attached by securing it to the sleeve 10 along a perforated line 15 such that after the receiver is secured within the sleeve, the manipulator portion may be separated from the sleeve. The manipulator 20 is detached with the fingers remaining within the finger extensions and used to protect the users hand from contact with the dial.

Figure 5:
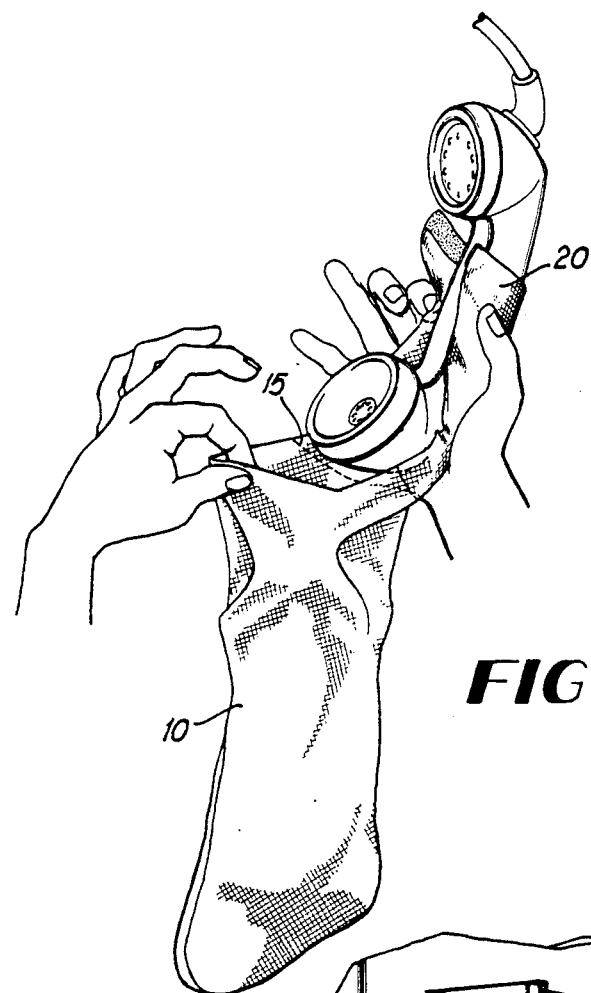
FIG. 5 illustrates an alternate embodiment of the disclosed device and shows a user depositing the telephone receiver into the sleeve portion of the present invention.
Figure 6:
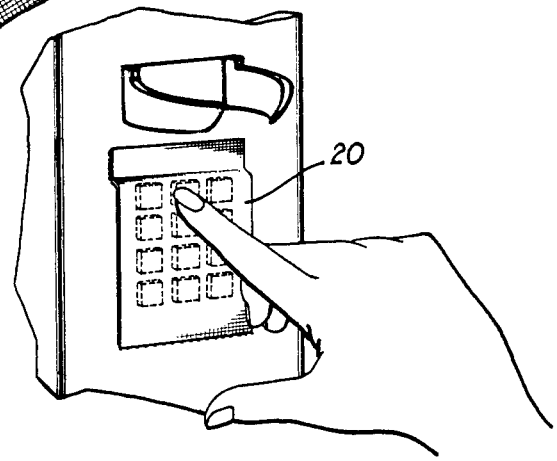
FIG. 6 illustrates the dialing procedure using the detached manipulating pad of the alternate embodiment to cover the dialing pad while dialing.

A second embodiment of the disclosed invention shown in FIG. 5 and 6 contemplates the manipulator 20 having a larger palm protecting portion without finger extensions protruding therefrom. The manipulator 20 is again releasably attached to the sleeve by perforations 15 at the joining line between the manipulator 20 and the sleeve 10. The palm protecting area is still used to grasp the telephone receiver, however, once the receiver is contained within the sleeve 10, the manipulator 20 is detached from the sleeve 10 and placed over the dial pad. A low sticking adhesive can be placed on the manipulator 20. The adhesive allows the manipulator to be maintained on the telephone while covering the dial pad. Dialing can be achieved through the manipulator 20 as it is placed over the pad.

The prophylactic device for use with the telephone can be made of a variety of materials with the only constraints being that the material must be thin enough or perforated so that the speaking voice and hearing are not impaired when using the telephone. The material should be foldable so that it may be carried in a small space and of such property that it does not crackle or make noises when flexed, as would, for example a sheet of writing paper. The material may also be transparent, the advantage being that a transparent prophylactic could also be used on telephones where a touch tone dialing pad is located on the inside of the receiver. Generally, clear plastic, soft cloth or tissue paper are all acceptable construction materials, cloth being reusable and washable, and tissue and plastic being disposable. The interior of the sleeve 10 may contain an antiseptic as an extra means of protection from dirt and germs emanating from the telephone receiver.

It is to be understood that the form of the invention herewith shown and described is to be taken as preferred examples of the same, and that various changes in the shape, size, material, arrangement and assembly method of parts may be resorted to without departing from the spirit of the invention or scope of the subjoined claims.

I claim:

1. A prophylactic device for protection from exposure to germs contained on a telephone receiver and dial pad comprising:
   (a) a sleeve having an open end, a closed end and a continuous wall connecting said open end and said closed end, said wall having interior and exterior sides, said sleeve being of appropriate length and width to envelop a telephone receiver;
   (b) a manipulator member having a front side and a back side, said manipulator member being detachably secured to and extending from the said sleeve at said open end where said front side is continually connected to said interior wall of said sleeve and said back side is continuously connected to the exterior wall of said sleeve, said manipulator member extending partially around the diameter of said open end of said sleeve and being of a size to protect a user's hand while grasping a telephone receiver.

2. A prophylactic device as defined in claim 1, wherein the interior wall of said sleeve is coated with an antiseptic solution.

3. A prophylactic device as defined in claim 1, wherein said manipulator member is releasably attached to said sleeve at said open end by a series of perforations extending between said manipulator member and said sleeve.

4. A prophylactic device as defined in claim 3, wherein said manipulator member is further comprised of coating on said front side of a low stick adhesive material such that said member is releasably attachable to a dialing pad of a telephone.

5. A prophylactic device as defined in claim 1, wherein said manipulator member is further comprised of a plurality of finger extensions attached to said manipulator member, said finger extensions being tubular, each having a closed top end, a bottom end attached to said manipulator member and an insert hole for inserting a finger disposed at said bottom end of said finger extension such that said insert hole is adjacent the back side of said manipulator member.

6. A prophylactic device as defined in claim 5, wherein said manipulator member is releasably attached to said sleeve at said open end by a series of perforations extending between said manipulating member and said sleeve.

7. A prophylactic device as defined in claim 1, wherein said device is made of a thin, flexible, soft material.

8. A prophylactic device as defined in claim 7 wherein said device is made of a transparent material.

* * * * *